US008246943B2

(12) United States Patent
Banerjee et al.

(10) Patent No.: US 8,246,943 B2
(45) Date of Patent: Aug. 21, 2012

(54) PREBIOTIC COMPOSITION

(75) Inventors: Gautam Banerjee, Bangalore (IN); Maxwell Oliver Bingham, Vlaardingen (NL); Deepak Ramachandra Mhasavade, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 293 days.

(21) Appl. No.: 12/774,806

(22) Filed: May 6, 2010

(65) Prior Publication Data

US 2010/0297058 A1 Nov. 25, 2010

(30) Foreign Application Priority Data

May 19, 2009 (EP) .................................... 09160656
Jan. 21, 2010 (IN) .......................... 0165/MUM/2010

(51) Int. Cl.
*A61K 31/765* (2006.01)
(52) U.S. Cl. .................................................... 424/78.37
(58) Field of Classification Search ........................ None
See application file for complete search history.

(56) References Cited

U.S. PATENT DOCUMENTS

| 5,071,653 | A | 12/1991 | Kakuda et al. | 424/195.1 |
|---|---|---|---|---|
| 2003/0069396 | A1 | 4/2003 | Nishimura et al. | 530/350 |
| 2006/0093725 | A1 | 5/2006 | Zhang | 426/597 |
| 2008/0075795 | A1 | 3/2008 | Hensley et al. | 424/729 |
| 2008/0085349 | A1 | 4/2008 | Chen | 426/534 |
| 2008/0119545 | A1 | 5/2008 | Hensley et al. | 514/456 |
| 2008/0234362 | A1 | 9/2008 | Chandler | 514/456 |

FOREIGN PATENT DOCUMENTS

| EP | 4 417 966 | 5/2004 |
|---|---|---|
| GB | 1 391 747 | 4/1975 |
| GB | 2 435 166 | 6/2007 |
| WO | 03/002126 | 1/2003 |
| WO | 2004/056205 | 7/2004 |
| WO | 2005/020699 | 3/2005 |
| WO | 2005/115170 | 12/2005 |
| WO | 2006/046122 | 5/2006 |
| WO | 2007/056432 | 5/2007 |
| WO | 2009/024429 | 2/2009 |

OTHER PUBLICATIONS

PCT International Search Report in a PCT application PCT/EP2010/054830, May 2010.
European Search Report in an EP application EP 09 16 0656, Oct 2009.
Lee et al., "*Effect of tea phenolics and their aromatic fecal bacterial metabolites on intestinal microbiota*", Research in Microbiology, 2006, vol. 157, pp. 876-884.
Besra et al., "*Antidiarrhoeal Activity of Hot Water Extract of Black Tea (Camellia sinensis)*", Phytotherapy Research, 2003, vol. 17, pp. 380-384.
Jafari et al., "*Black tea extract and its major polyphenolic pigment may ameliorate the gastrointestinal disorder in irritable bowel syndrome*", Medical Hypotheses, 2006, vol. 67, p. 419).
Zvetkova et al., "*Aqueous extract of Crinum latifollum(L.) and Camellia sinensis show immunomodulatory properties in human peripheral blood mononuclear cells*", International Immunopharmacology, 2001, vol. 1, pp. 2143-2150.
Chanudhuri et al."*Prokinetic Effect of Black Tea on Gastronitestinal Motility*", Life Sciences, 2000, vol. 66. No. 9, pp. 847-854.
Lakenbrink et al., "*Flavonoids and Other polyphenols in Consumer Brews of Tea and Other Caffeinated Beverages*", Journal of Agriculture Food Chemistry, vol. 48, 2000. pp. 2848-2852.
Miller et al., "*An in vitro method for estimation of iron availability from meals$^{1-3}$*", The American Journal of Clinical Nutrition, vol. 34, Oct. 1961. pp. 2248-2256.
Macfarlane et al., "*Validation of a Three-State compound Continuous Culture System for Investigating the Effect of Retention Time on the Ecology and Metabolism of Bacteria in the Human Colon*", Microbial Ecology, 1998, vol. 35, pp. 180-187.
Tzounis et al., "*Flavanol monomer-induced changes to the human faecal microflora*", British Journal of Nutrition, 2007, pp. 1-11.
Matsuki et al., "*Use of 16S rRNA Gene-Targeted Group-Specific Primers for Real-Time PCR Analysis of Predominant Bacterial in Human Feces*", Applied and Environmental Microbiology, Dec. 2004, vol. 70, No. 12, pp. 7220-7228.
Weatherby, "*Tea May Enhance Intestinal Health and Immunity*", Jan. 2007, Vital Choices Newsletter, vol. 4, No. 123, pp. 1-3.
Gato, et al. "*The influence of Tea Catechins on Fecal Flora of Elderly Residents in Long-Term Care Facilities*", Annals of Long-Term Care, 1998, vol. 6, No. 2, pp. 43-48.
Hata, "*Influence of Tea Catechins on the Digestive Tract*", Journal of Cellular Biochemistry Supplement, 1997, vol. 27, pp. 52-58.
Mai et al., "*Effects of a Controlled Diet and Black Tea Drinking on the Fecal Microflora Composition and the Fecal Bile Acid Profile of Human Volunteers in a Double-Blinded Randomized Feeding Study*", Journal of Nutrition, 2004, vol. 134, pp. 473-478.
Lee et al., "*Inhibition of Pathogenic Bacterial Adhesion by Acidic Polysaccharide from Green Tea (Camellia sinensis)*", Journal of Agricultural and Food Chemistry, 2006, vol. 54, pp. 8717-8723.
Friedman "*Overview of antibacterial, antitoxin, antiviral, and antifungal activities of tea flavonoids and teas*", Mol. Nutrition Food Res., 2007, vol. 51, pp. 116-134.
Krutmann, "*Pre- and probiotics for human skin*", Journal of Dermatological Science, vol. 54, (2009), pp. 1-5.

*Primary Examiner* — Bethany Barham
(74) *Attorney, Agent, or Firm* — Ellen Plotkin

(57) ABSTRACT

The present invention provides for use of a composition comprising black tea flavonoids as a prebiotic and/or for the treatment or prevention of conditions associated with poor gut health or low immunity. The flavonoids comprise thearubigin in an amount of at least 82% by weight of the tea flavonoids. Also provided is an edible product comprising the black tea flavonoids.

7 Claims, No Drawings

PREBIOTIC COMPOSITION

TECHNICAL FIELD OF THE INVENTION

The present invention relates to a prebiotic composition. In particular the present invention relates to a prebiotic composition comprising black tea flavonoids.

BACKGROUND OF THE INVENTION

Gastrointestinal health is a major concern of consumers in both developed and developing countries from the point of view of daily gastrointestinal comfort and also resistance to or prevention of acute and chronic diseases such as infectious diarrhoea and inflammatory bowel diseases. There is a demand for products that can be consumed on a daily basis that can provide such benefits.

Currently available strategies to address these concerns include probiotic products wherein liquids (typically dairy-based drinks) containing one or a number of strains of beneficial bacteria are consumed to derive a benefit such as improved gut health and/or improved natural defences. This approach is limited since it requires the products to be chilled (to maintain viability of the bacteria that provide the benefit), and questions remain over its efficacy since the bacteria must pass through the harsh acidic environment of the stomach and reach the colon in sufficient numbers to provide the intended effects. Furthermore, such considerations mean that probiotic products are typically expensive for the consumer and require a complex supply chain to effectively deliver them.

An alternative strategy is the use of prebiotics wherein food components are given that have a beneficial health effect through their selective metabolism in the intestinal tract. Typical targets for such an approach are bifidobacteria and lactobacilli (i.e. common probiotic species) since they are generally regarded as safe, are commonly found in breast fed infants in high numbers, alter the intestinal environment through the production of short chain fatty acids meaning that pathogens cannot colonise, produce antimicrobial components that target pathogens, may improve the immune status of the host and may reduce inflammation of the colon associated with poor modern diets. Currently available prebiotics include fructans such as inulin and fructo-oligosaccharides and these have been shown to significantly increase bifidobacteria in humans.

Prebiotics do not suffer from questions over their viability in the way probiotics do and they can be formulated into a number of product formats without loss of viability. However, in certain aspects, current prebiotics are difficult to formulate into common foodstuffs owing to their impact on product taste (fructans can be slightly sweet) and structure (they can change mouthfeel). Furthermore, products are often required to be formulated with higher than the effective amount of prebiotic owing to the fact that fructans can suffer degradation during pasteurisation, baking, sterilisation and similar processes. These considerations mean that prebiotic-containing processed food products remain expensive and thus limited to only a small number of customers because of price.

Thus a demand exists from consumers for an affordable solution wherein benefits can be provided in the arena of gut health, resistance to infectious diseases and/or prevention of chronic gastrointestinal diseases.

Tea has been consumed in one form or another for over 4000 years and is now popular in both developed and developing countries. Tea is popular for a number of reasons: it is generally regarded as healthy, it can be a safe alternative to untreated water and is associated with benefits such as relaxation, mental alertness and has a widely acceptable taste. The low price of tea also means that it can be consumed by consumers in all socio-economic groups.

Several documents suggest that consumption of black tea and/or components thereof can have positive effects on the health of the consumer. For example, US 2008/119545 A and US 2008/075795 A (both in the name of C. HENSLEY & S. PYO) disclose methods and compositions for preventing and treating Avian Influenza utilizing an effective quantity of an ingredient having a composition selected from the group consisting of theaflavin, theaflavin-3,3'-digallate, theaflavin-3-monogallate, theaflavin-3 gallate, theaflavin-3'-gallate, thearubigin, gallic acid, tannic acid, (−)-epigallocatechin gallate (EGCG), (−) epigallocatechin (EGC), (+)-epicatechin (EC), (−)-gallocatechin gallate (GCG), and catechin.

It has also been suggested that black tea and/or components thereof can have positive effects on gut function and/or health. For example, K. Jafari et al (*Medical Hypotheses*, 2006, 67(2), p. 419) discloses that black tea extract and its major polyphenolic pigment may ameliorate the gastrointestinal disorder in irritable bowel syndrome; and L. Chaudhuri et al (*Life Sciences*, 2000, 66(9), pp. 847-854) discloses that a hot water extract of black tea significantly accelerated the gastrointestinal transit (GIT) in vivo in mice.

Compositions comprising black tea components in combination with conventional prebiotics are also known. For example, WO 2007/056432 A (PERQUE INC) discloses compositions comprising one or more prebiotics (e.g., one or more dietary fibers) in combination with selenium compounds, flavonoids and/or flavonols, and phosphatides; and US 2008/085349 A (Z. Y. CHEN) discloses a beverage comprising tea components and a non-digestible health sweetener (VitaSugar® IMO).

It has also been recognised that black tea and/or components thereof can have a positive influence on gut microflora. U.S. Pat. No. 5,071,653 (ITOEN LTD) discloses substantially flavorless extracts from the leaves of *C. sinensis* which promote the growth of bifidobacteria. The compositions are provided by extracting water or ethanol-soluble solids from *C. sinensis* leaves with a polar organic solvent that is immiscible with water. There is no evidence in U.S. Pat. No. 5,071,653 that the extracts disclosed therein have a true prebiotic effect (i.e. that promotion of the growth of bifidobacteria is in preference to promotion of the growth of pathogenic bacteria such as clostridia). Furthermore, the extracts disclosed therein are substantially flavourless and thus are presumably devoid of the flavonoids (such as thearubigin) which give black tea its distinctive taste.

WO 2004/056205 A (UNILEVER) discloses the use of a cooked food product comprising black tea leaves, an extract of black tea or a mixture thereof, to maintain or improve microflora balance and/or to treat or prevent diarrhoea in a subject consuming the composition and wherein the black tea leaves or the extract of black tea is/are present in an unbound state.

We have now found that the flavonoid components of black tea have a significant prebiotic effect. Furthermore we have identified that black tea flavonoids having a specific composition are especially effective prebiotics and thus may be expected to be especially effective at delivering the health benefits associated with consumption of prebiotics, such as treatment or prevention of a gastrointestinal condition, and/or treatment or prevention of a condition associated with sub-optimal immunity. We have also found that these black tea flavonoids have improved immunomodulatory capability compared to whole tea extracts.

TESTS AND DEFINITIONS

Prebiotic

As used herein, the term "prebiotic" refers to a substance consumed orally by an individual to beneficially affect that individual by selectively stimulating the growth and/or activity of one or more of a limited number of bacteria in the colon of the individual. The preferred prebiotics are those which selectively stimulate the growth and/or activity of bifidobacteria and/or lactic acid bacteria. Even more preferred are those which stimulate the growth and/or activity of bifidobacteria and/or lactic acid bacteria in preference to pathogenic bacteria such as clostridia.

Black Tea

As used herein, the term "tea" refers to material from the leaves and/or stem of Camellia sinensis var. sinensis and/or Camellia sinensis var. assamica. "Black tea" refers to tea wherein the leaves and/or stem have been subjected to a so-called "fermentation" step wherein they are oxidised by certain endogenous enzymes. This oxidation may even be supplemented by the action of exogenous enzymes such as oxidases, laccases and peroxidases.

Flavonoids, Thearubigin and Catechins

Definitions and analytical methods for determining flavonoids and thearubigin can be found in Christiane Lakenbrink, Svenja Lapczynski, Beate Maiwald, and Ulrich H. Engelhardt. *J. Agric. Food Chem.*, 2000, 48 (7), 2848-2852. In brief, total flavonoids and thearubigin in a composition can be calculated by the following relations (1) and (2):

$$\text{Total flavonoids(wt \%)} = TP - (GA + TG + CQA) \quad (1),$$

$$\text{Thearubigin (wt \%)} = \text{Total flavonoids} - (C + TF + FOG + FAG) \quad (2),$$

wherein TP is the percentage of total phenolics by weight of the composition; GA is the percentage of gallic acid by weight of the composition; TG is the percentage of theogallin by weight of the composition; CQA is the percentage of cholorogenic acids by weight of the composition; C is the percentage of catechins by weight of the composition; TF is the percentage of theaflavins by weight of the composition; FOG is the percentage of flavonol glycosides (expressed as aglycons) by weight of the composition; and FAG is the percentage of flavone glycosides (expressed as aglycons) by weight of the composition.

Comprising

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above. Moreover, the term "comprises" is meant to encompass the terms "consisting essentially of" and "consisting of".

SUMMARY OF THE INVENTION

In a first aspect, the present invention provides the use of a composition comprising black tea flavonoids as a prebiotic wherein the flavonoids comprise thearubigin in an amount of at least 82% by weight of the tea flavonoids.

Surprisingly we have found that compositions wherein the amount of thearubigin in the black tea flavonoids is at least 82% by weight of the flavonoids are especially effective as prebiotics. Thus the invention may also be said to relate to a method of producing a prebiotic effect in an individual, the method comprising administering to the individual a composition comprising an effective amount of black tea flavonoids wherein the flavonoids comprise thearubigin in an amount of at least 82% by weight of the tea flavonoids.

In a further aspect, the present invention relates to the use of the black tea flavonoids in combating conditions which are associated with a poor immune system and/or poor gut health. Thus the invention provides use of a composition comprising black tea flavonoids in the manufacture of a medicament for the treatment or prevention of a condition associated with sub-optimal immunity and/or of a gastrointestinal condition, wherein the flavonoids comprise thearubigin in an amount of at least 82% by weight of the tea flavonoids.

In a still further aspect, the present invention relates to an edible product which is adapted for administration in the methods and uses of the invention. Thus the invention provides an edible product having a mass of less than 500 g and comprising black tea flavonoids in a mass of greater than 0.2 g, wherein the black tea flavonoids comprise thearubigin in an amount of at least 82% by weight of the tea flavonoids.

DETAILED DESCRIPTION

Prebiotic and Immunomodulatory Uses and Methods

In one aspect of the present invention, a composition comprising black tea flavonoids is administered to an individual in order to produce a prebiotic effect in the individual. The resulting prebiotic effect, i.e. the selective stimulation of the growth and/or activity of one or more of a limited number of bacteria may beneficially affect the health of the individual in one or more ways.

For example, administration of the composition may be used to treat or prevent a condition associated with sub-optimal immunity. The condition associated with sub-optimal immunity is preferably selected from the common cold, influenza, chronic inflammation, allergy or a combination thereof.

Additionally or alternatively, administration of the composition may treat or prevent a gastrointestinal condition. The gastrointestinal condition is preferably selected from inflammatory bowel disease, irritable bowel syndrome, infectious diarrhoea, environmental enteropathy or a combination thereof.

The composition may additionally or alternatively be administered for the removal or alleviation of visceral pain.

The composition is administered orally.

The composition comprises an effective amount of the black tea flavonoids. In particular the amount of black tea flavonoids administered to the individual on a daily basis should be enough to produce a noticeable selective (prebiotic) effect in the gut microflora of the individual. Surprisingly, we have found that administration of 2.4 g of black tea solids can produce a similar prebiotic effect to that of administration of 5 g of chicory inulin. Black tea solids comprise around 20-40% by weight of flavonoids. Thus it is preferred that the composition is administered to the individual in an amount to provide at least 0.2 g black tea flavonoids per day, more preferably at least 0.4 g black tea flavonoids per day and most preferably at least 0.6 g black tea flavonoids per day. Furthermore these results suggest that large amounts of black tea flavonoids need not be administered in order to achieve the prebiotic effect. Thus it is preferred that the composition is administered to the individual in an amount to provide at most 5 g black tea flavonoids per day, more preferably at most 3 g black tea flavonoids per day and most preferably at most 1.5 g black tea flavonoids per day.

Black Tea Flavonoids

The black tea flavonoids for use in the compositions, uses, edible products, leaf tea products and methods of the present invention are enriched in thearubigin. In particular we have found that when the black tea flavonoids comprise at least 82% by weight thearubigin, an especially pronounced prebiotic and/or immunomodulatory effect is achievable. Thus the black tea flavonoids comprise thearubigin in an amount of at least 82% by weight of the tea flavonoids, preferably in an amount of at least 84% by weight of the tea flavonoids.

Typically the black tea flavonoids will comprise non-thearubigin components such as theaflavins and/or catechins. Thus the amount of thearubigin in the black tea flavonoids may be less than 99.99% by weight of the black tea flavonoids, or even less than 98% by weight of the black tea flavonoids. It is especially preferred that amount of catechins in the black tea flavonoids is limited, as catechins appear to reduce the prebiotic effect of thearubigins. Thus it is preferred that the flavonoids comprise catechins in an amount of less than 12% by weight of the flavonoids, more preferably in an amount of less than 10% by weight of the flavonoids, more preferably still less than 8%, and most preferably from 0.01 to 6%. Additionally or alternatively, the black tea flavonoids may comprise less than 3% theaflavins by weight of the tea flavonoids as we have found that theaflavins have little or no prebiotic effect. More preferably the black tea flavonoids comprise less than 1.5% theaflavins by weight of the black tea flavonoids, more preferably still less than 0.5% and most preferably from 0.0001 to 0.1%.

Edible Product

In a preferred aspect of the present invention, the composition is administered to the individual in the form of an edible product.

The edible product may be a food. For example, the product may be a margarine, low fat spread, confectionery product (such as chocolate), ice cream, yoghurt, dressing, mayonnaise, sauce, bakery product, shortening, soup or cheese. However, it is especially preferred that the edible product is a beverage, most preferably a tea-based beverage.

The edible product comprises sufficient black tea flavonoids to provide that a prebiotic effective dose of the flavonoids can be achieved without having to consume a large number of the products in a single day. Thus the product comprises black tea flavonoids in a mass of greater than 0.2 g, preferably greater than 0.4 g, and most preferably at least 0.6 g. However, the product need not comprise large amounts of black tea flavonoids. In particular it is preferred that the mass of black tea flavonoids in the product is at most 10 g, more preferably at most 3 g, and most preferably at most 1.5 g.

The mass of the product should not be so large that an excessive amount of product is required to be consumed on a daily basis. Thus the edible product has a mass of less than 500 g, preferably less than 450 g, more preferably from 50 to 350 g.

Because black tea flavonoids can influence the colour and/or taste of an edible product, it is preferable to employ the flavonoids in a limited concentration range. In particular it is preferred that the concentration of black tea flavonoids is from 0.15 to 10% by weight of the product, more preferably from 0.2 to 4%.

The edible product may be manufactured in any suitable way, however in a preferred embodiment the edible product is manufactured using a method comprising:

(a) providing an edible matrix; and
(b) combining the edible matrix with a substance comprising black tea flavonoids, wherein the edible matrix and the substance are combined in a weight ratio of at least 2 parts edible matrix to 1 part black tea flavonoids.

This method allows for separately manipulating the properties of the edible matrix and black tea flavonoids before combination. Furthermore, the higher proportion of edible matrix than black tea flavonoids allows for minimisation of the impact of the black tea flavonoids on taste and/or colour of the edible matrix.

The substance is preferably a water-soluble black tea extract or fraction thereof. The extract or fraction may be in the form of a solid (e.g. powder) or liquid. The substance preferably has a thearubigin content of at least 20% by dry weight of the substance, more preferably from 25 to 100%.

The edible matrix may be any foodstuff or food ingredient or combination thereof. In particular the matrix be an edible liquid, solid or gel. The matrix may be an aqueous composition i.e. contains greater than 50% water by weight of the matrix. Alternatively the matrix may be substantially non-aqueous. The matrix may optionally be in the form of an oil-in-water or a water-in-oil emulsion.

Preferably the matrix and substance are combined in step (b) in a weight ratio of at least 10 parts edible matrix to 1 part black tea flavonoids, more preferably in the range from 20:1 to 500:1.

Leaf Tea

Another aspect of the invention relates to a leaf tea which is suitable for preparing beverages which have an effective amount of the black tea flavonoids as described herein. Thus there is provided a leaf tea product comprising black tea flavonoids in a mass of greater than 0.2 g, wherein the black tea flavonoids comprise thearubigin in an amount of at least 82% by weight of the tea flavonoids.

The leaf tea product comprises sufficient black tea flavonoids to provide that a prebiotic effective dose of the flavonoids can be achieved without having to prepare a large number of beverages in a single day. Thus the leaf tea product comprises black tea flavonoids in a mass of greater than 0.2 g, preferably greater than 0.4 g, and most preferably at least 0.6 g. However, the leaf tea product need not comprise large amounts of black tea flavonoids. In particular it is preferred that the mass of black tea flavonoids in the leaf tea product is at most 5 g, more preferably at most 1.5 g, and most preferably at most 0.8 g.

The mass of the leaf tea product is preferably sufficient to prepare a single-serve beverage. For example, the amount of the leaf tea may be from 0.5 to 5 g, more preferably from 1 to 4 g, and most preferably from 1.5 to 3.5 g. It is especially preferred that the amount of leaf tea is packaged in an infusion package, such as a tea bag.

EXAMPLES

The present invention will now be illustrated by reference to the following non-limiting examples.

Example 1

This example demonstrates the prebiotic effect of black tea extract as compared with green tea extract and non-flavonoid tea components (polyphenol-free tea extract).

Materials

Black Tea Extract Spray-dried solids from aqueous extraction of commercial black leaf tea (Lipton® Yellow Label from Unilever UK Ltd).

Green Tea Extract Commercial green tea powder (Ceytea™ from Premium Exports Ceylon Ltd).

Polyphenol-free Tea Extract Ceytea™ green tea powder (14 g) was dissolved in 500 ml freshly boiled deionised water using an Ultra Turrax™ homogeniser. The resulting solution was poured into a 5 l plastic beaker containing 3.5 l deionised water and mixed using an overhead paddle stirrer. To the solution was added 54 g polyvinylpolypyrrolidone (Polyclar® 10) powder and the mixture stirred vigorously for 10 minutes. The resulting slurry was centrifuged at 8000 rpm for 30 min in four equal portions using a Beckman™ JLA 9100 rotor. The supernatants were recombined and tested for residual polyphenols with Folins reagent. Some residual polyphenols remained hence the solution was again treated with 54 g Polyclar® 10 powder and centrifuged. The supernatants were again combined and filtered under vacuum through a Whatman™ 541 filter. The resultant solution was analysed and found to contain 60 mg/l polyphenols and a solids content of 0.17%. The solution was rotary evaporated to 150 ml and then freeze dried. The whole process was repeated three times to yield enough solid matter.

Digestion of Tea Extracts

Black tea, green tea and polyphenol-free tea extracts were digested as described by Miller et al (*American Journal of Clinical Nutrition*, 1981, 34, pp. 2248-2256). Digestion was performed anaerobically (10% $H_2$, 10% $CO_2$, 80% $N_2$) to minimize oxidation of polyphenols. Samples were freeze-dried following digestion.

Gut Model

Experiments were performed in a 3 stage in vitro gut model according to the method described in Macfarlane et al (*Microb. Ecol.*, 1998, 35(2) pp. 180-187) and microbial changes were assessed according to the methods described in Tzounis at al (*Br. J. Nutr.*, 2007, doi: 10.1017/S0007114507853384, pp. 1-11) or Matsuki et al (*Appl. Environ. Microbiol.*, 2004, 70(12), pp. 7220-7228). The amount of digested tea extract added to each gut model was equivalent to that resulting from consumption of 6 cups of tea per day (assuming 0.4 g of total undigested tea solids per cup). These amounts are given in table 1.

TABLE 1

| Substrate | Quantity added per day(g) | Equivalent quantity before digestion (g per day) |
|---|---|---|
| Digested black tea extract | 1.33 | 2.40 |
| Digested green tea extract | 1.16 | 2.40 |
| Polyphenol-free tea extract | 0.51 | 1.60* |

*calculated assuming ⅓ of the total tea solids are lost in polyphenol removal.

Inulin was also included in the study as a positive control and was added in a dose of 5 g per day.

Fermentations first proceeded to a steady state condition (SS1) without the test substrate added. At this point, bacterial populations were monitored. After this, the test substrate was added daily and the fermentation continued to a further steady state (SS2) where the same analyses were performed. All enumerations refer to Log 10 cells/ml of culture fluid.

Results

Table 2 details the bacterial populations in the vessels at SS1 and SS2.

TABLE 2

| Substrate | SS | Vessel No | Bifidobacteria | Bacteroides | Clostridia (C. histolyticum and C. perfringens) | Eubacterium rectale and Clostridium coccoides |
|---|---|---|---|---|---|---|
| Black Tea Extract | 1 | 1 | 6.05 | 8.57 | 9.46 | 9.68 |
| | | 2 | 6.31 | 8.96 | 9.37 | 9.60 |
| | | 3 | 6.52 | 9.70 | 9.06 | 9.08 |
| | 2 | 1 | 7.87 | 8.42 | 9.29 | 9.42 |
| | | 2 | 7.99 | 8.76 | 9.23 | 9.41 |
| | | 3 | 8.10 | 9.68 | 8.90 | 9.21 |
| Green Tea Extract | 1 | 1 | 6.67 | 7.25 | 6.56 | 9.02 |
| | | 2 | 6.46 | 8.25 | 6.47 | 8.96 |
| | | 3 | 6.60 | 8.43 | 6.06 | 8.83 |
| | 2 | 1 | 7.37 | 7.95 | 6.70 | 9.02 |
| | | 2 | 6.87 | 7.70 | 6.35 | 9.04 |
| | | 3 | 6.61 | 8.18 | 5.79 | 8.76 |
| Inulin | 1 | 1 | 7.62 | 7.23 | 5.67 | 9.14 |
| | | 2 | 7.52 | 8.53 | 5.84 | 9.19 |
| | | 3 | 7.49 | 8.35 | 5.49 | 9.17 |
| | 2 | 1 | 8.45 | 6.36 | 5.89 | 9.37 |
| | | 2 | 8.26 | 8.81 | 5.49 | 9.28 |
| | | 3 | 8.15 | 8.55 | 5.59 | 9.20 |
| Polyphenol-Free Tea Extract | 1 | 1 | 6.44 | 8.88 | 6.39 | 8.96 |
| | | 2 | 6.64 | 8.89 | 6.57 | 8.96 |
| | | 3 | 6.70 | 8.69 | 6.62 | 8.86 |
| | 2 | 1 | 5.93 | 8.79 | 6.72 | 8.76 |
| | | 2 | 5.97 | 8.76 | 7.25 | 8.67 |
| | | 3 | 6.11 | 8.34 | 6.70 | 8.45 |

The results in table 2 illustrate that the only tea extract which consistently increased the population of bifidobacteria in preference to the other bacteria (compare values between SS1 & SS2 for the same vessel) was the black tea extract. This prebiotic effect was achieved via the addition of 1.33 g digested tea solids per day (equivalent to ingestion of 6 cups/day) whilst 5 g/day chicory inulin achieved a similar effect.

The effect was not achieved when digested polyphenol-free tea extract was added to the model. In fact the data in table 2 illustrate that the non-polyphenol constituents of tea actually decrease the population of bifidobacteria in the gut. This indicates that tea flavonoids and in particular black tea flavonoids act as prebiotics.

Example 2

This example demonstrates the prebiotic effect of various black tea extracts and black tea components.

Preparation of BTE and Fraction F 900 kg of Lipton® Yellow Label black tea leaves were subjected to counter-current extraction at a leaf to water weight ratio of 1:20 and at a water temperature of 95° C. The resulting liquor was centrifuged to remove suspended solids and the liquid filtered through a ceramic membrane and concentrated using a combination of ultrafiltration and reverse osmosis condensation. The concentrated extract was ultra high temperature sterilised and spray dried to produce 180 kg of black tea extract powder (BTE).

150 g of BTE was mixed and dissolved in 2 l of 70% acetone (aqueous). This resulted in the recovery of 112 g of 70% acetone (aqueous) soluble material following evaporation of the acetone. 100 g of this material was dissolved in 2 l of deionised water and subjected to 4×1 l extraction with methyl isobutyl ketone (MiBK). This resulted in MiBK soluble material and an aqueous layer. This aqueous layer was further subjected to extraction with 4×1 l ethylacetate which resulted in ethylacetate soluble material and a further aqueous layer. This further aqueous layer was then extracted with 2×0.5 l n-butanol. The n-butanol layer was taken and after evaporation of n-butanol, 10.5 g of n-butanol soluble material were recovered (Fraction F). All extraction and solvent evaporation procedures were performed under vacuum to avoid or minimize oxidative damage of phenolic material.

Preparation of Fractions SI, SII and TB

Instant Kenyan black tea powder was obtained from DAMIN Foodstuff (Zhangzhou) Co Ltd; ethanol, ethyl acetate, butanol, $NaHCO_3$ and polyamide were obtained from Sinopharm Chemical Reagent Co, Shanghai, Ltd; and XAD1600 (macroporous resin) was obtained from Rohm and Haas.

Black tea powder (216 g) was dissolved in 2500 ml of deionised water and heated at 80° C. for 30 minutes. The solution was cooled in an ice bath for 10 minutes and filtered through cotton to obtain a clear solution. To remove caffeine and other potential impurities, the solution was loaded onto a pre-prepared polyamide column (4 l volume, Diameter× Length=20 cm×130 cm), and eluted with deionised water (8 l, flow rate: 4 l/hour) to remove caffeine, followed by elution with 95% ethanol to elute other material remaining on the column. Following evaporation of the ethanol, ~70 g of powdered product was recovered. To partition this product, 60 g of product was dissolved in 600 ml of deionised water at 80° C. for 30 minutes and extracted with ethyl acetate (2×600 ml) to obtain two fractions: EA fraction and water fraction (W1).

To obtain fraction SI, the EA fraction (1200 ml) was extracted with 2.5% aqueous $NaHCO_3$ (2×1200 ml) to obtain two further fractions: EA fraction and 2.5% $NaHCO_3$ fraction. The 2.5% $NaHCO_3$ fraction was adjusted to pH 7 using acetic acid and then loaded onto a pre-prepared XAD1600 column (1 l, diameter×length=20 cm×35 cm). A first elution was performed with deionised water to remove salts and a second elution was performed with 95% ethanol to obtain SI solution. After evaporation to remove ethanol, 13 g of a fraction designated SI was obtained.

To obtain fractions SII and TB, the water fraction W1 was extracted with butanol (2×600 ml) to obtain two further fractions: butanol fraction, (which after evaporation of butanol resulted in 22.5 g of a fraction designated SII), and water fraction, (which after evaporation resulted in a fraction designated TB, 9.2 g).

Compositional Analysis

Total phenolics (TP) were determined according to the method given in the international standard ISO 14502-1:2005 ("Determination of substances characteristic of green and black tea—Part 1: Content of total polyphenols in tea—Colorimetric method using Folin-Ciocalteu reagent").

Catechins (C), theogallin (TG), gallic acid (GA) and alkaloids were determined according to the method given in the international standard ISO 14502-2:2005 ("Determination of substances characteristic of green and black tea—Part 2: Content of catechins in green tea—Method using high-performance liquid chromatography").

Theaflavins (TF), flavonol glycosides (FOG) and chlorogenic acids (CQA) were determined using the methods in Lakenbrink et al., (*J. Agric. Food Chem.*, 2000, 48 (7), 2848-2852). Briefly:

TF was determined by HPLC (isocratic with 23% acetonitrile in 2% acetic acid, aq) with Detection at 375 nm and calibration against authentic standards of known purity.

FOG was determined by HPLC after clean-up by polyamide column chromatography and calibration against each of myricetin (myricitrin), quercetin (rutin) and kaempferol glycoside.

CQA was determined by HPLC after clean-up by SPE on RP-18 and calibration against 5-CQA and p-coumaric acid standards.

The amount of flavone C glycosides (FAG) was not measured as the amounts were assumed to be very small compared with the other flavonoids.

Batch Culture Fermentations

Several series of in vitro anaerobic, stirred, pH controlled batch culture fermentations inoculated with faecal microbiota were used to investigate the prebiotic potential of the tea fractions. The general method used can be found in Tzounis et al., (*Br. J. Nutr.*, 2007, doi: 10.1017/S0007114507853384, pp. 1-11). The model conditions were chosen such that the environmental conditions located in the distal region of the human large intestine were mimicked. The comparison of the fractions was based on the enumeration over time (24 hours) of selected target bacterial groups (bifidobacteria, *Clostridium coccoides—Eubacterium rectale, Clostridium leptum* and bacteroides) via RT-Q-PCR measurements (according to Matsuki et al (*Appl. Environ. Microbiol,* 2004, 70(12), pp. 7220-7228)).

The following materials were purchased for use in the experiments: chicory inulin (Beneo-Orafti), peptone water, bile salts (no. 3), yeast extract PBS (Dulbecco A pH 7.3) (Oxoid Ltd, Basingstoke, Hampshire, UK), L-cysteine-HCl, hemin, vitamin K1, $KH_2PO_4$, NaCl (Sigma Aldrich, Germany), $CaCl_2.6H_2O$, $NaHCO_3$ (Fluka chemie, GmbH) $K_2HPO_4$, $MgSO_4.7H_2O$ (Merck, Germany), Tween 80 (VWR), resazurin (Brocades Stheeman & Pharmaica, Netherlands).

All fermentations were performed in 300 ml batch fermentors with water jackets. Each batch fermentor was filled with 180 ml basal nutrient medium. The medium contained the following ingredients: peptone water (2 g/l), yeast extract (2 g/l), NaCl (0.1 g/l), $K_2HPO_4$ (0.04 g/l), $KH_2PO_4$ (0.04 g/l), $MgSO_4.7H_2O$ (0.01 g/l), $CaCl_2.6H_2O$ (0.01 g/l), $NaHCO_3$ (2 g/l), Tween 80 (2 ml/l), hemin (0.5 g/l), vitamin $K_1$ (10 µl/l), L-cysteine (0.5 g/l), bile salts (sodium glycocholate and sodium taurocholate) (0.5 g/l) and resazurin (0.25 g/l). The media was adjusted to pH 7.0, aliquoted into respective vessels and autoclaved at 121° C. for 15 minutes. The batch fermentations were gassed overnight with oxygen-free nitrogen (15 ml/hr). Prior to inoculation, the media was readjusted to pH 7.0.

Immediately prior to the addition of faecal slurry, a selected substrate was added to each fermentor. The following substrates were assessed at 1% w/v addition:
chicory inulin (acting as positive control),
0% carbohydrate addition (blank acting as a negative control),
Tea fractions SI, SII, TB, F, and BTE.

The temperature of each batch fermntation was maintained at 37° C. by means of a circulating water bath and medium pH was maintained at 6.8 via a pH controller (Electrolab, UK). The batch fermentations were inoculated with 20 ml of fresh faecal slurry (1/10 w/v) respectively, and continuously sparged with $O_2$-free $N_2$ at a flow rate of 15 ml/min. Batch cultures were ran for a period of 72 hours and samples were obtained at t0, t18, t24, t48 and t72 hours from each vessel for selected bacterial groups by real-time Q-PCR. Each sample was centrifuged (36220 g) for 3 minutes to obtain a pellet for use in DNA extraction. The following functional bacterial groups were analysed: *Bifidobacterium* spp. *Bacteroides fragilis* group, *Clostridium coccoides* group, *Clostridium leptum* group and *Lactobacillus* spp.

Analysis of Data

In an attempt to rank the substrates in terms of selectivity for bifidobacteria, a parameter was developed denoted as PR. This attempts to quantify the extent to which bifidobacteria are selected for by the substrate under investigation whilst accounting for the changes induced purely by the media, and the starting levels of each functional bacterial group (e.g. those assessed by RT-Q-PCR) in comparison to the effects induced on the community (inoculum) by the positive control (inulin). In this way it is possible to compare across fermentations inoculated with different faecal inocula and thus isolate the effects of the substrate on selectivity for bifidobacteria. PR is calculated according to equation (3):

$$PR_s = 10(X_s - X_0)/X_1 \quad (3),$$

wherein $X_s$ is a parameter indicating the selective increase of bifidobacteria in the batch culture to which substrate s was added, $X_0$ is a parameter indicating the selective increase of bifidobacteria in the batch culture to which 0% carbohydrate was added (negative control) and $X_1$ is a parameter indicating the selective increase of bifidobacteria in the batch culture to which inulin was added (positive control).

For each culture the parameter X is calculated according to formula (4):

$$X = \Delta N_{Bif} - \Delta N_{Ccoc} - \Delta N_{Clep} - \Delta N_{Lac} - \Delta N_{Bac} \quad (4),$$

wherein $\Delta N_{Bif}$ is the relative increase in *Bifidobacterium* spp., $\Delta N_{Ccoc}$ is the relative increase in *Clostridium coccoides/ Eubacterium rectale* group, $\Delta N_{Clep}$ is the relative increase in *Clostridium leptum* group, $\Delta N_{Lac}$ is the relative increase in *Lactobacillus* spp., and $\Delta N_{Bac}$ is the relative increase in *Bacteroides fragilis* group.

The relative increase of a given bacterial group in a given culture ($\Delta N$) is calculated according to formula (5):

$$\Delta N = (N_{24}/N_0)/(Tot_{24}/Tot_0) \quad (5),$$

wherein $N_{24}$ is the number of cells of the bacterial group per ml of culture fluid after 24 hours of fermentation, $N_0$ is the number of cells of the bacterial group per ml of culture fluid at the start of fermentation, $Tot_{24}$ is the total number of all bacterial cells per ml of culture fluid after 24 hours of fermentation, and $Tot_0$ is the total number of all bacterial cells per ml of culture fluid at the start of fermentation.

Thus values of PR above zero indicate selectivity for bifidobacteria. Larger numbers indicate greater selectivity. A value of 10 indicates selectivity equivalent to the positive control. Values below zero indicate no selectivity for bifidobacteria.

Results

The composition of the tea fractions BTE, TB, SI, SII and F is given in Table 3 (% by weight of powder).

TABLE 3

| Tea Fraction | TP | GA | TG | CQA | Total Flavonoids | C | TF | FOG | TR |
|---|---|---|---|---|---|---|---|---|---|
| BTE | 32.85 | 0.84 | 1.44 | 0.92 | 29.66 | 5.26 | 0.92 | 0.97 | 22.52 |
| TB | 46.93 | 0.06 | 0.06 | 0 | 46.81 | 1.07 | 0.03 | 0.39 | 45.32 |
| F | 32.56 | 0.39 | 1.27 | 0.39 | 30.51 | 1.62 | 0 | 2.97 | 25.93 |
| SI | 46.64 | 0.04 | 0.02 | 0 | 46.57 | 5.88 | 0 | 3.27 | 37.41 |
| SII | 55.74 | 0.07 | 0.07 | 0 | 55.6 | 5.2 | 0 | 4.79 | 45.61 |

The prebiotic effect of these tea fractions and correlation of this effect with flavonoid composition is illustrated by the data in Table 4.

TABLE 4

| Fraction (Substrate) | Prebiotic effect (PR) | Thearubigins (wt % of Total Flavonoids) | Catechins (wt % of Total Flavonoids) | Flavonol glycosides (wt % of Total Flavonoids) |
|---|---|---|---|---|
| F | 4.87 | 84.99 | 5.31 | 9.73 |
| TB | 4.05 | 96.82 | 2.29 | 0.83 |
| SII | 2.1 | 82.03 | 9.35 | 8.62 |
| BTE | 1.88 | 75.93 | 17.73 | 3.27 |
| SI | −0.7 | 80.33 | 12.63 | 7.02 |

The data in table 4 indicate that the greatest prebiotic effect is seen with those black tea fractions wherein thearubigin is present in an amount of at least 82% by weight of the flavonoids (fractions SII, TB and F). Furthermore it is apparent that the black tea fractions wherein the flavonoids contain the largest amounts of catechins have the lowest prebiotic effect.

Example 3

This example demonstrates the immunity benefit of various black tea extracts and black tea components.

The γδT cell is one of the important members of immunity network. Activation of this cell type is implicated in better immune response. Evaluation of one cell surface protein i.e. Vγ2δ2 indicate the activation of γδT cells. Hence induction of higher amount of vγ2δ2 cells by an inducer indicates higher potency as an immunomodulator.

Protocol

Whole blood from 3 human volunteers (v-1, V-2 and V-3) was incubated with the tea fractions for 12 days with addition of IL-12 on every 3rd days. Post 12 days incubation, the level of v$\square$2$\square$2/CD3 (marker for $\square\square$T cells) cells were evaluated by flow cytometry using standard protocol. The data is expressed as % V$\square$2$\square$2/CD3 cells in the whole blood. The results were compared with that of untreated (vehicle treated) control as well as that of whole tea extract. Increased level of V$\square$2$\square$2/CD3 cells compared to that of whole tea extract indicates higher immunomodulatory capability than whole tea. The experiments were done using blood of 3 different donors.

Results

The tea was fractions used were as described in Example 2 except that fraction SII was not tested.

The results for various fractions are tabulated in Table 5.

TABLE 5

| Fraction (Substrate) | % V$\square$2$\square$2/CD3 | | | $\square\square$ T cell activity |
|---|---|---|---|---|
| | V-1 | V-2 | V-3 | |
| Untreated | 15.6 | 5.8 | 19.7 | − |
| F | 50.1 | 68.7 | 98.7 | + |
| TB | 40 | 30.7 | 93.5 | + |
| BTE | 35.7 | 21.2 | 92.2 | − |
| SI | 16.3 | 4.5 | 30.3 | − |

+ High Activity
− Low activity

The data in table 5 indicate that the greatest immunity benefit is seen with those black tea fractions wherein thearubigin is present in an amount of at least 82% by weight of the flavonoids (fractions F and TB).

The invention claimed is:

1. A method producing a prebiotic effect in an individual, said method comprising:
    administering to said individual a composition comprising black tea flavonoids in an amount greater than about 0.2 g black tea flavonoids per day;
    wherein said tea flavoinoids comprise thearubigin in an amount of at least 82% and catechins in an amount of about 0.01 to about 6% by weight of said tea flavonoids.

2. The method as claimed in claim 1, wherein said individual has a condition of common cold, influenza, chronic inflammation and/or allergy.

3. The method as claimed in claim 1, wherein said individual has a condition of selected form the group consisting of inflammatory bowel disease, irritable bowel syndrome, environmental enteropathy, and infectious diarrhea.

4. The method as claimed in claim 1 wherein the composition is administered to an individual in an amount of at least about 0.4 g black tea flavonoids per day.

5. An edible product having a mass of less than about 500 g and comprising black tea flavonoids in a mass of greater than about 0.2 g, wherein the black tea flavonoids comprise thearubigin in an amount of at least 82% and catechins in an amount of about 0.01 to about 6% by weight of the tea flavonoids; and
    wherein said edible product comprises leaf tea.

6. An edible product as claimed in claim 5 wherein the mass of black tea flavonoids is greater than about 0.4 g.

7. An edible product as claimed in claim 5 wherein the mass of the product is less than about 450 g.

* * * * *